United States Patent [19]

Shipp et al.

[11] 3,941,853

[45] Mar. 2, 1976

[54] SUBSTITUTED POLYNITRO-DIPHENYLMETHANES

[75] Inventors: Kathryn G. Shipp; Lloyd A. Kaplan, both of Silver Spring, Md.

[73] Assignee: The United States of America as represented by the Secretary of the Navy, Washington, D.C.

[22] Filed: June 25, 1969

[21] Appl. No.: 871,220

Related U.S. Application Data

[62] Division of Ser. No. 644,434, May 29, 1967, Pat. No. 3,574,758.

[52] U.S. Cl. ......... 260/645; 260/465 R; 260/465 E; 260/465 G; 260/465 H; 260/578; 260/646
[51] Int. Cl.² ................... C07C 79/10; C07C 79/12
[58] Field of Search.... 260/645, 646, 465 R, 465 E, 260/465 G, 465 H, 578

[56] References Cited
UNITED STATES PATENTS 3,006,972    10/1961    Fields et al. .................... 260/645 X

OTHER PUBLICATIONS

Gehrig et al., Anal. Chem., Vol. 37, pp. 868 to 872 (1965).

*Primary Examiner*—Leland A. Sebastian

[57] ABSTRACT

A polynitro-benzophenone having at least 4 nitro substituents and useful as a high energy explosive composition. A polynitro-diphenylmethane intermediate which may be oxidized to provide the aforesaid benzophenones. A process for preparing the aforesaid intermediate and the process for oxidizing the aforesaid intermediate to the benzophenone.

20 Claims, No Drawings

SUBSTITUTED POLYNITRO-DIPHENYLMETHANES

This application is a division of application Ser. No. 644,434, filed May 29, 1967, now U.S. Pat. No. 3,574,758.

BACKGROUND OF THE INVENTION

This invention relates to new compositions of matter and more particularly to both a new class of polynitro-substituted benzophenones having 4 or more nitro groupings, and to a new class of polynitro-diphenylmethanes. This invention further relates to a process for preparing the aforesaid benzophenones from the aforesaid diphenylmethanes, and to the process of preparing the aforesaid diphenylmethanes.

SUMMARY OF THE INVENTION

It is an object of this invention to provide a new composition of matter having utility as a high energy explosive. More particularly, it is an object of this invention to provide a novel polynitro-substituted benzophenone having the following structure:

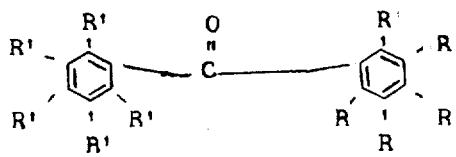

wherein each R and R' is a radical selected from the group consisting of nitro, halo, hydro, lower alkyl, cyano, amino, phenyl, nitrophenyl, alkylphenyl, halonitrophenyl, styryl, nitrostyryl, halonitrostyryl, benzyl, nitrobenzyl, halonitrobenzyl and combinations thereof, providing that at least three R' radicals and at least one R radical are nitro;

and to provide a diphenylmethane intermediate having the following structure;

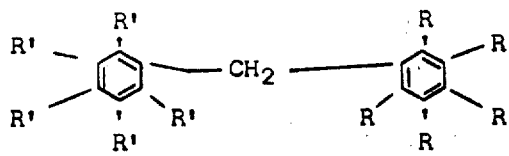

wherein R and R' is defined as above. Diphenylmethane compounds are also known as "ditans".

DESCRIPTION OF THE PREFERRED EMBODIMENTS

Due to the high nitrogen-oxygen content of the benzophenone compositions of this invention, they are particularly well adapted for use as high energy explosives. Also, since they are generally characterized by high thermal stability, even at temperatures as high as 300°C, and since they possess medium range impact sensitivity, they are particularly well suited for use in propellant booster compositions.

Prior to this invention, polynitrosubstituted ditans of less than four nitro groups were prepared by straight nitration of diphenylmethane with a mixture of nitrate acids. By the present invention however, nitro substituted benzophenones having more than four nitro groups, and more particularly five or more nitro groups, may be prepared by strongly oxidizing a polynitrodiphenylmethane of the type prepared by reacting an aromatic halo compound with a alkyl or dialkylbenzene, such as trinitrotoluene (TNT).

Accordingly, from 0.25 to 6.0 moles of an alkylbenzene may be contacted with an excess quantity of an alkoxide, such as potassium or sodium hydroxide dissolved in methyl or ethyl alcohol, to form the corresponding benzyl anion which is then reacted with the aromatic halo compound to provide the substituted diphenylmethane. Oxidation of the ditan provides the novel benzophenones.

Any aromatic halo composition having at least one nitro group is suitable for present purposes. Preferred, however, are those in which the halo is selected from the group consisting of chloro, bromo or fluoro, such as picryl chloride, 1-chloro-2,6-dinitrobenzene, 1-chloro-2,4-dinitrobenzene, 4-chloro-3,5-dinitrobenzonitrile, 3-chloro-2,2',4,4',6,6'-hexanitrostilbene, 3-chloro-2,2',4,4',6,6'-hexanitrobiphenyl, 3,3'-dichloro-2,2',4,4',6,6'-hexanitrobiphenyl, 1,3-dibromo-2,4,6-trinitrobenzene and 1-fluoro-2,6-dinitrobenzene.

The temperature of reaction is not critical and is dependent only on the nature of the reactants which, due to their high nitro content, are often explosive at high temperatures. Consequently, ambient temperatures or temperatures slightly above ambient are generally desirable.

In preparing the anion, it is normally convenient to use a compatible solvent such as tetrahydrofuran, acetonitrile or nitrobenzene with an alkoxide.

Reaction between the anion and the aromatic halo is usually complete within about twenty to forty minutes, after which the reaction is quenched in a cold dilute acid solution, such as dilute hydrochloric acid, causing the diphenylmethane to precipitate in a fine crystalline form which may be readily separated. Although the ditans are considered for the purposes of this invention as intermediates in the formation of the substituted benzophenones, it should be understood that they also possess independent utility as high explosives although of somewhat lower thermal stability and lower impact sensitivity than the benzophenones.

In preparing the ditan, it has been found desirable in order to obtain maximum yields, to include a small quantity of dimethylsulfoxide. While it is not understood precisely why the sulfide increases yield, it is believed that there is some effect in increasing the reactivity of the benzyl anion by causing desolvation. For this purpose from 0.1 to 2 parts by volume sulfide per part of solvent is normally sufficient.

Oxidation of the substituted ditan to a substituted benzophenone is effected by treating the ditan with a strong oxidizing agent in an oxidizing acid solution. While the choice of neither the oxidant nor acid is critical, best results are obtained when using chromium trioxide in a 3:1 to 1:3 molar solution of nitric acid in oleum.

A preferred embodiment for effecting oxidation is to admix the ditan with an excess quantity of oxidant in a solution of the oxidizing acid while maintaining the temperature between about 30°–70°C. Normally, reaction will be substantially complete within a few hours as will be evidenced by the formation of a fine crystalline precipitate.

Representative of the substituted benzophenones which may be prepared by the methods of this invention are, 2,2',4,4',6-pentanitrobenzophenone, 2,2',4-,4',6 hexanitrobenzophenone, 3-(2,4,6-trinitrostyryl)-2,2',4,4',6,6'-hexanitrobenzophenone, 3-(2,4,6-trinitrophenyl)-2,2',4,4',6,6'-hexanitrobenzophenone, 3-bromo-2,2',4,4',6,6'-hexanitrobenzophenone, 3-chloro-3'-(2,4,6-trinitrophenyl)-2,2',4,4',6,6'-hexanitrobenzophenone, and 4-cyano-2,2',4',6,6'-pentanitrobenzophenone.

Representative of the substituted ditan intermediates of this invention are, 2,2',4,4',6,6'-hexanitrodiphenylmethane, 2,2',4,6,6'-pentanitrodiphenylmethane, 3-(2,4,6-trinitrobenzyl)-2,2',4,4',6,6'-hexanitrostilbene, 3-chloro-3',-(2,4,6-trinitrobenzyl)-2,2',4-,4',6,6'-hexanitrobiphenyl and 3-bromo-2,2',4,4',6,6'-hexanitrodiphenylmethane.

Having generally described the invention the following examples are presented for purposes of illustration and are not intended to be restrictive in any manner.

EXAMPLE I 2,2',4,4',6,6'-Hexanitrodiphenylmethane, "Hexaditan"

To a solution of 4.5 g (0.02 mole) of TNT in 50 ml of tetrahydrofuran at ambient temperature in a 400 ml beaker was added rapidly, with vigorous stirring, 10 ml (0.02 mole) of an 11.2% methanolic solution of potassium hydroxide. There was immediate formation of a dark red-brown solid in the solution. Immediately after the addition of the methanolic potassium hydroxide a solution of 2.5 g (0.01 mole) of picryl chloride in 25 ml of dimethylsulfoxide was added to the mixture. A deep blue color developed rapidly and darkened almost to black during the reaction period, accompanied by a slight temperature rise (to ca 30°) and a lessening of the amount of solid present in the mixture. Stirring was continued for thirty minutes and then the reaction was quenched by pouring the mixture into 750 ml of cold water containing 25 ml of concentrated hydrochloric acid. An orange yellow precipitate formed which gradually crystallized and was then filtered off. This precipitate was extracted with portions of hot methanol until the methanol extracts were almost colorless and the residue was light yellow in color. The methanol insoluble product was filtered off, washed further with methanol and dried in an oven at 80°. The product was then redissolved in 35 ml of acetonitrile. This solution was filtered and 50 ml of hot methanol was added causing recrystallization of the fine, pale yellow, almost colorless needles, mp 228°–230°C. Recrystallization resulted in raising the melting point to 230°C. Ultimate yield was 4.0 gm, 91% of theoretical yield.

Hexaditan is soluble in acetone, acetonitrile, dimethylsulfoxide, tetrahydrofuran and hot glacial acetic acid, but almost insoluble in methanol, chloroform and ether. Anal. Calcd for $C_{13}H_6N_6O_{12}$: C, 35.6; H, 1.4; N, 19.2; mol wt, 438. Found: C, 35.5; H, 1.5; N, 18.9, 18.9; mol wt. 430,439 (Osmometer, acetonitrile solution).

EXAMPLE II 2,2',4,4',6-Pentanitrodiphenylmethane, "2,4-Pentaditan"

1.9 gm (0.01 moles) of 1-fluoro-2,4-dinitrobenzene was substituted for the picryl chloride of Example I and the procedure repeated. The yield of crude product was 3.3 g, or 84% of the theoretical yield. Recrystallized yielded 2.95 g, or 75% of theoretical yield of pale yellow crystals, mp 208°–210°(dec). Anal. Calcd for $C_{13}H_7N_5O_{10}$: C, 39.7; H, 1.8; N, 17.8; mol wt, 393. Found: C, 39.5, 39.6; H, 2.0, 1.7; N, 17.7, 17.6; mol wt, 388 (Osmometer, acetonitrile solution).

EXAMPLE III 2,2',4,4',6-Pentanitrodiphenylmethane ("2,4-Pentaditan")

With 6g (0.03 mole) of 1-chloro-2,4-dinitrobenzene and 4.5 g (0.02 mole) of TNT, i.e. a mole ratio of halide to TNT of 1.3, the crude product wieghed 2.7 g or 35% (on basis of TNT used) of the theoretical yield, and infrared spectrum showed only 2,4-Pentaditan, to be present.

EXAMPLE IV 2,2',4,6,6'-Pentanitrodiphenylmethane, "2,6-Pentaditan"

With the mole ratio of reactants, 2,6-dinitrochlorobenzene/TNT equal to 6, i.e. 24 g (0.12 mole) of 2,6-dinitrochlorobenzene to 4.5 g (0.02 mole) of TNT, the procedure of Example I was repeated and 2.75 g, or 35% of the theoretical yield (based on TNT) of the 2,6-Pentaditan was obtained. Recrystallized from acetonitrile-methanol-water formed pale yellow needles, mp 188°–190°(dec). Anal. Calcd for $C_{13}H_7N_5O_{10}$: C, 39.7; H, 1.8; N, 17.8; mol wt, 393. Found: C, 39.9, 39.6; H, 2.0, 1.9; N, 18.2, 18.2.

EXAMPLE V

4-Cyano-2,2',4',6,6'-Pentanitrodiphenylmethane "4-Cyanopentaditan"

The crude yield of product from 2.3 g (0.01 mole) of 4-chloro-3,5-dinitrobenzonitrile was 2.25 g or 54% of the theoretical yield, from which 1.8 g, 43% of theoretical, of fine, faintly yellow needles were obtained by recrystallization, mp 205°(dec). The product was very sensitive to light, becoming yellow rapidly and greenish yellow on prolonged exposure. Anal. Calcd for $C_{14}H_6N_6O_{10}$: C, 40.2; H, 1.5; N, 20.1. Found: C, 40.7; H, 1.6, 1.5; N, 20.0, 19.7.

EXAMPLE VI

3-Bromo-2,2',4,4',6,6'-hexanitrodiphenylmethane

The reaction of 3.75 g (0.01 mole) of 1,3-dibromo-2,4,6-trinitrobenzene with 4.5 g (0.02 mole) of TNT was carried out as Example I. The crude product was fairly soluble in methanol, very soluble in THF, acetone and acetonitrile. After extraction with methanol at ambient temperature the oily crude was dissolved in acetone, methanol was added and the solution was evaporated on a hot plate with magnetic stirring until crystals formed. This crystalline product was filtered off and dried. It weighed 1.5 g, or 29% of theoretical yield. After decolorization with Darco in THF solution, the solution was diluted with methanol and the product was precipitated by the addition of water. An oil formed which slowly hardened to a colorless solid. Recrystallized from acetone-methanol by evaporation to small volume it formed very fine crystals, mp 170°–172° (dec). Anal. Calcd for $C_{13}H_5N_6O_{12}$ Br: N, 16.3; Br, 15.5. Found: N, 16.2, 16.1; Br, 15.5, 15.5.

EXAMPLE VII

3-(2,4,6-Trinitrobenzyl)-2,2',4,4',6,6'-hexanitrostilbene

The reaction of 4.5 g (0.02 mole) of TNT with 4.6 g (0.01 mole) of 3-chloro-2,2',4,4',6,6'-hexanitrostilbene was carried out as in the above reactions. The crude reaction product, after extraction with methanol was a brittle mass which was dissolved in 50 mol of acetonitrile, diluted with an equal volume of methanol and heated on a hot plate with magnetic stirring. Light yellow crystals separated and were filtered off, washed well with methanol and dried. This material weighed 4.8 g, 71% of the theoretical yield, melted at 168°–170° (dec), and elemental analysis showed that it contained a mole of acetonitrile. Calcd for $C_{23}H_{12}N_{10}O_{18}$: N, 19.6. Found: N, 19.7, 19.4. Recrystallized from 50 ml of THF with 50 ml of methanol added to the hot THF solution after filtering, the product separated in very fine, almost colorless crystals, mp 210°–211°C. Anal. Calcd for $C_{21}H_9N_9O_{18}$: C, 37.2; H, 1.3; N, 18.8. Found: C, 37.5, 37.7; H, 1.6, 1.5; N, 19.0, 18.4.

EXAMPLE VIII

3-(2,4,6-Trinitrobenzyl)-2,2',4,4',6,6'-hexanitrobiphenyl

The reaction of 4.5 g (0.02 mole) of TNT with 4.6 g, (0.01 mole) of 3-chloro-2,2',4,4',6,6'-hexanitrobiphenyl was carried out as above. After extracting the crude reaction product with methanol until the extracts were light colored, the somewhat gummy residue was dissolved in acetone, an equal volume of methanol was added and the solution was heated, with magnetic stirring, on a hot plate. A light yellow crystalline material separated, was filtered off and dried. It weighed 1.7 g, 25% of the theoretical yield. Recrystallized from acetone methanol formed faintly yellow rod-like crystals, mp 255°–256°. Anal. Calcd for $C_{19}H_7N_9O_{18}$: C, 35.1; H, 1.1; N, 19.4. Found: C, 34.9, 34.2; H, 1.6, 1.2; N, 19.2, 18.8.

EXAMPLE IX

3-Chloro-3'-(2,4,6-trinitrobenzyl)-2,2'4,4',6,6'-hexanitrobiphenyl

The reaction of 4.5 g (0.02 mole) of TNT with 4.9 g (0.01 mole) of 3,3'-dichloro-2,2',4,4',6,6'-hexanitrobiphenyl was carried out as above. The reaction product was worked up in a manner similar to that for the preparation of 3-(2,4,6-trinitrobenzyl)-2,2',4,4',6,,6'-hexanitrobiphenyl and yielded 2.0 g, a 29% yield, of crude product. Recrystallized from acetone methanol formed fine, almost colorless crystals, mp 252°C. Anal. Calcd for $C_{19}H_6N_9O_{18}Cl$: N, 18.4; Cl, 5.2. Found: N, 18.4, 18.6; Cl, 5.5, 5.4.

Many of the above reactions were also carried out without the use of dimethylsulfoxide by dissolving the halogen compound in tetrahydrofuran instead of dimethylsulfoxide. Generally yields were from 40 to 70% lower with the exception of the reaction of 1-chloro-2,4,6-trinitrobenzene which was unaffected.

EXAMPLE X

2,2',4,4',6-Pentanitrobenzophenone

A solution of 5.0 gm of the product resulting from Example II was placed in 35 ml of 90% nitric acid in a 100 ml, 3-neck round bottom flask equipped with a thermometer and a mechanical stirrer. To this solution was added 25 ml of 30% oleum, keeping the temperature under 50° by the rate of addition with cooling in an ice bath as needed. After the addition of the oleum was completed, 3.0 g of chromium trioxide was added. The reaction mixture was then heated to 50°–60° by means of a water bath for two hours. At the end of the reaction period the mixture consisted of a dark green solution containing a considerable quantity of very fine needle-like crystals. After cooling to ambient temperature this mixture was poured over flaked ice, the precipitated product was collected on a filter, washed first with water, then methanol and dried. It weighed 4.75 g, or 92% of the theoretical yield. Recrystallized from nitrobenzene it formed very fine, almost colorless needles, mp 320°–322°.

EXAMPLE XI

2,2',4,4',6,6'-Hexanitrobenzophenone

The procedure of example X was repeated using 2,2',4,4',6,6'-hexanitrodiphenylmethane as prepared in example I. A 92% yield of 2,2',4,4',6,6'-hexanitrobenzophenone mp 280°–282°. Anal. Calcd for $C_{13}H_4N_6O_{13}$: C, 34.55; H, 0.89; Found: C, 34.62, 34.24; H, 0.97, 0.81; N, 18.19, 18.37.

Any one of 2,2',4,6,6'-pentanitrobenzophenone, 3-bromo-2,2',4,4',6,6'-hexanitrobenzophenone, 3-(2,4,6,-trinitrophenyl)-2,2',4,4',6,6'-hexanitrobenzophenone, 3-(3-chloro-2,4,6-trinitrophenyl)-2,2',4,4',6,6'-hexanitrobenzophenone, 3-(2,4,6-Trinitrostyryl)-2,2',4,4',6,6'-hexanitrobenzophenone, may be obtained by the methods of example XI.

The following Table shows the impact sensitivity of the products of this invention in comparison with those explosives previously available. Impact sensitivities were determined on the Bruceton ERL machine using a 2.5 kg weight and type 12 tools with the material on sandpaper. Measurements are recorded as the 50% minimum height in which a 2.5 kilogram weight will cause at least one explosion in 20 drops.

TABLE

Comparison of Impact Sensitivity

| Compound | Impact Sensitivity |
|---|---|
| 2,2',4,4',6-pentanitrobenzophenone | 54 cm |
| 2,2',4,4',6,6'-hexanitrodiphenylmethane "Hexaditan" | 39 cm |
| 2,2',4,4',6,6'-hexanitrostilbene | 39 cm |
| 2,2',2'',4,4',4'',6,6',6''-Nonanitroterphenyl "NONA" | 39 cm |
| 2,2',2'',2''',4,4',4'',4''',6,6',6'',6'''-Dodecanitro-m,m'-quaterphenyl "Dodeca" | 29 cm |

Various modifications of the invention can be made by one skilled in the art, in view of the above disclosure, without departing from the spirit and scope of the invention.

What is claimed as new and desired to be secured by Letters Patent of the United States is:

1. The substituted ditan of the formula,

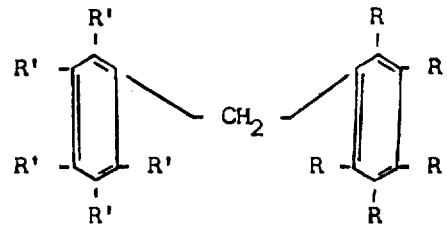

wherein each R and R' is a radical selected from the group consisting of nitro, halo, hydrogen, lower alkyl, cyano, amino, phenyl, nitrophenyl, alkylphenyl, halonitrophenyl, styryl, nitrostyryl, halonitrostyryl, benzyl, nitrobenzyl, halonitrobenzyl and mixtures thereof providing that at least one R radical and at least three R' radicals are nitro.

2. The ditan of claim 1 wherein at least two R radicals are nitro.

3. The ditan of claim 1 being 2,2',4,4',6-pentanitrodiphenylmethane.

4. The ditan of claim 1 being 2,2',4,4',6,6'-hexanitrodiphenylmethane.

5. The ditan of claim 1 being 4-cyano-2,2',4',6,6'-pentanitrodiphenylmethane.

6. The ditan of claim 1 being 3-(2,4,6-trinitrobenzyl)-2,2',4,4',6,6'-hexanitrostilbene.

7. The ditan of claim 1 being 3-(2,4,6-trinitrobenzyl)-2,2',4,4',6,6'-hexanitrobiphenyl.

8. The ditan of claim 1 being 3-chloro-3'-(2,4,6-trinitrobenzyl)-2,2',4,4',6,6'-hexanitrobiphenyl.

9. The ditan of claim 1 being 3-bromo-2,2',4,4',6,6'-hexanitrodiphenylmethane.

10. The ditan of claim 1 wherein two R' radicals are hydrogen and three R' radicals are nitro.

11. The process of preparing the ditan of claim 10 which comprises reacting an aromatic halide of the formula

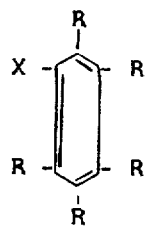

wherein X is halogen from the group consisting of Cl, F, and Br and wherein R is a radical selected from the group consisting of nitro, halo, hydro, lower alkyl, cyano, amino, phenyl, nitrophenyl, alkylphenyl, halonitrophenyl, styryl, nitrostyryl, halonitrobenzyl and mixtures thereof with trinitrotolnene in an alkoxide solution.

12. The process of claim 11 wherein the alkoxide is the reaction product of methanol and potassium hydroxide.

13. The process of claim 11 wherein the reaction is conducted in a solution of dimethylsulfoxide and tetrahydrofuran.

14. The process of claim 11 wherein the aromatic halide is picryl chloride.

15. The process of claim 11 wherein the aromatic halide is 4-chloro-3,5-dinitrobenzonitrile.

16. The process of claim 11 wherein the aromatic halide is 3-chloro-2,2',4,4'6,6'-hexanitrostilbene.

17. The process of claim 11 wherein the aromatic halide is 3-chloro-2,2',4,4',6,6'-hexanitrobiphenyl.

18. The process of claim 11 wherein the aromatic halide is 3-3'-dichloro-2,2',4,4',6,6'-hexanitrobiphenyl.

19. The process of claim 11 wherein the aromatic halide is 1,3-dibromo-2,4,6-trinitrobenzene.

20. The process of preparing the ditan of claim 1 which comprises reacting, in an alkoxide solution, a nitro-substituted aromatic halide of the formula

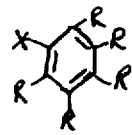

wherein X is a halogen, selected from the group consisting of Cl, F, and Br with a nitro substituted alkyl benzene of the formula

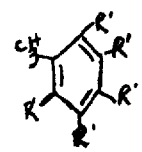

wherein each R and R' is a radical selected from the group consisting of nitro, halo, hydrogen, lower alkyl, cyano, amino, phenyl, nitrophenyl, alkylphenyl, halonitrophenyl, styryl, nitrostyryl, halonitrostyryl, benzyl, nitrobenzyl halonitrobenzyl and mixtures thereof; with the proviso that at least one R radical and at least three R' radicals are nitro.

* * * * *